United States Patent
Joly et al.

(10) Patent No.: US 11,692,206 B2
(45) Date of Patent: Jul. 4, 2023

(54) PRODUCTION OF AROMATICS BY REVERSE WATER GAS SHIFT, FERMENTATION AND RECYCLING TO PYROLYSIS

(71) Applicant: IFP Energies Nouvelles, Rueil-Malmaison (FR)

(72) Inventors: Jean-Francois Joly, Rueil-Malmaison (FR); Frederic Feugnet, Rueil-Malmaison (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 78 days.

(21) Appl. No.: 17/484,185

(22) Filed: Sep. 24, 2021

(65) Prior Publication Data

US 2022/0098624 A1    Mar. 31, 2022

(30) Foreign Application Priority Data

Sep. 29, 2020    (FR) .................... 20/09.871

(51) Int. Cl.
*B01D 3/14*       (2006.01)
*B01D 11/04*      (2006.01)
(Continued)

(52) U.S. Cl.
CPC .............. *C12P 7/06* (2013.01); *B01D 3/143* (2013.01); *B01D 11/0488* (2013.01);
(Continued)

(58) Field of Classification Search
CPC . C12P 7/06; C12P 7/065; B01D 3/143; B01D 11/0488; B01D 11/0492; B01J 19/245; B01J 2219/0004; C10G 61/02; C10G 2300/4006; C10G 2300/4012; C10G 2300/4018; C10G 2400/30; C10G 1/02; C10G 3/00; C10G 7/00; C10G 45/58;
(Continued)

(56) References Cited

U.S. PATENT DOCUMENTS 10,099,974 B2    10/2018    Bilaus et al.
10,961,464 B2     3/2021    Feugnet et al.
(Continued)

OTHER PUBLICATIONS

French Search Report dated Jun. 9, 2021 issued in corresponding FR 2009871 application (2 pages).

*Primary Examiner* — Randy Boyer
*Assistant Examiner* — Juan C Valencia
(74) *Attorney, Agent, or Firm* — Millen White Zelano & Branigan, PC; Brion P. Heaney

(57) ABSTRACT

Device and process for the conversion of a feedstock of aromatic compounds, in which the feedstock is treated notably by means of a fractionation train (4-7), a xylene separation unit (10) and an isomerization unit (11), and in which a pyrolysis unit (13) treats a second hydrocarbon feedstock, produces a pyrolysis effluent feeding the feedstock, and produces a pyrolysis gas comprising CO, $CO_2$ and $H_2$; a reverse water gas shift RWGS reaction section (50) treats the pyrolysis gas and produces an RWGS gas enriched in CO and in water; a fermentation reaction section (52) treats the RWGS gas enriched in CO and in water, to produce ethanol and recycle the ethanol to the inlet of the pyrolysis unit.

21 Claims, 1 Drawing Sheet

(51) Int. Cl.
  *B01J 19/24*  (2006.01)
  *C10G 61/02*  (2006.01)
  *C10K 3/02*  (2006.01)
  *C12M 1/00*  (2006.01)
  *C12P 7/06*  (2006.01)

(52) U.S. Cl.
  CPC ......... *B01D 11/0492* (2013.01); *B01J 19/245* (2013.01); *C10G 61/02* (2013.01); *C10K 3/026* (2013.01); *C12M 21/12* (2013.01); *B01J 2219/0004* (2013.01); *C10G 2300/4006* (2013.01); *C10G 2300/4012* (2013.01); *C10G 2300/4018* (2013.01); *C10G 2400/30* (2013.01)

(58) Field of Classification Search
  CPC ........ C10G 1/002; C10K 3/026; C12M 21/12; Y02E 50/10; Y02P 20/00; Y02P 30/20; C07C 5/2708; C07C 6/126; C07C 7/005; C07C 7/04; C07C 7/12
  See application file for complete search history.

(56) References Cited

U.S. PATENT DOCUMENTS

2016/0304788 A1* 10/2016 Sorensen ............. C10G 29/205
2017/0362143 A1 12/2017 Bilaus et al.
2020/0255744 A1 8/2020 Feugnet et al.

* cited by examiner

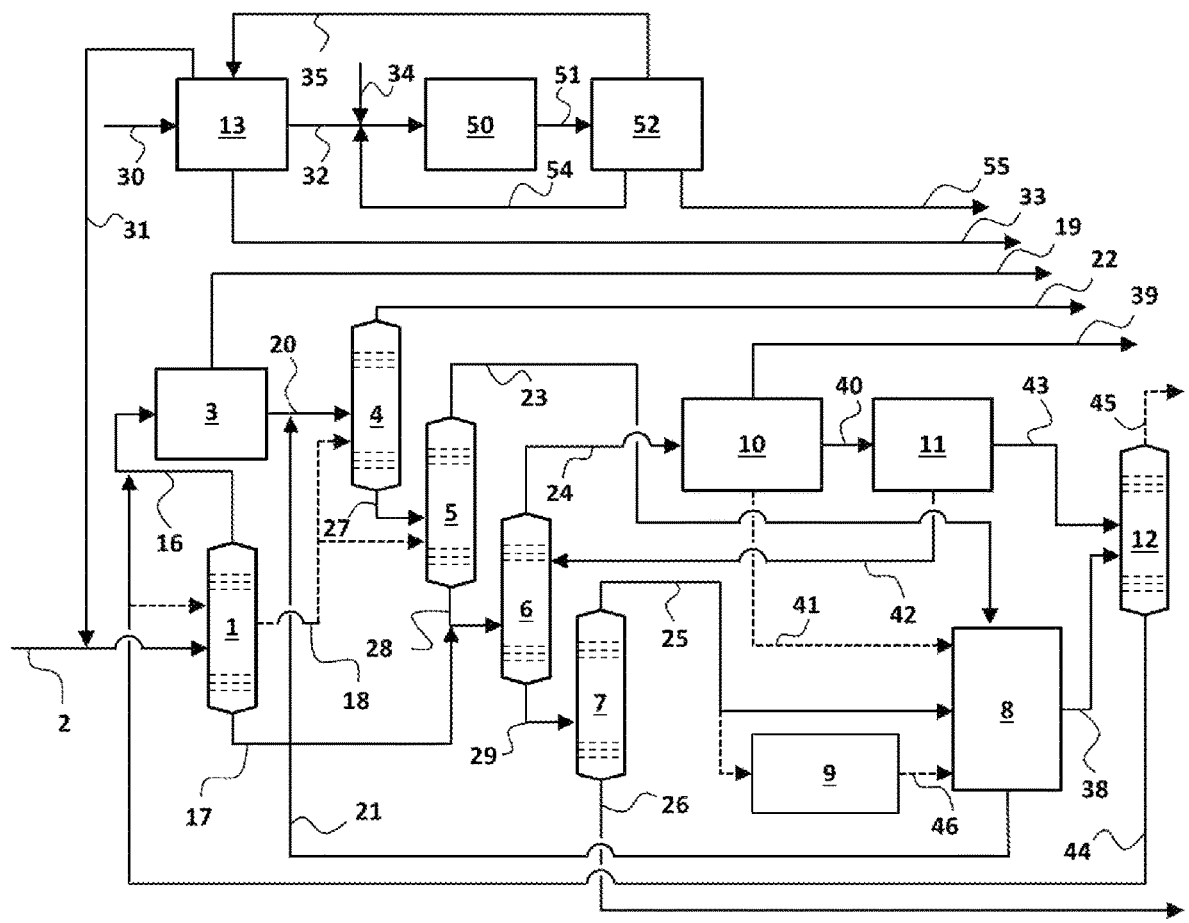

US 11,692,206 B2

PRODUCTION OF AROMATICS BY REVERSE WATER GAS SHIFT, FERMENTATION AND RECYCLING TO PYROLYSIS

TECHNICAL FIELD

The invention relates to the production of aromatics for the petrochemical industry (benzene, toluene and xylenes, i.e. BTX). More particularly, the object of the invention is to be able to increase the production of aromatics, and notably para-xylene, produced by a process for the pyrolysis of hydrocarbon compounds, and preferably of biomass, by conversion of the CO and $CO_2$ by-products of the pyrolysis, it being possible for all the carbon and in particular the biobased carbon to thus be upgraded.

An aromatic complex (or device for the conversion of aromatic compounds) is a device fed with feedstocks predominantly composed of six to ten carbon atoms or more, referred to as C6 to C10+ feedstocks. Various sources of aromatic compounds may be introduced into an aromatic complex, the most widespread being obtained from a process for the catalytic reforming of naphtha.

Within an aromatic complex, whatever the source of aromatics, benzene and alkylaromatics (e.g. toluene, para-xylene, ortho-xylene) are extracted therefrom and are then converted into desired intermediates. The products of interest are aromatics with 0 (benzene), 1 (toluene) or 2 (xylenes) methyl groups, and in particular, among the xylenes, para-xylene, having the greatest market value.

Processes for the pyrolysis of hydrocarbon compounds produce aromatic compounds but also a lot of CO and $CO_2$ as conversion by-products. When the pyrolysis is catalytic, the combustion of the coke present on the catalyst used in the pyrolysis reactor also produces a significant amount of $CO_2$.

PRIOR ART

To date, aromatic complexes make it possible to produce benzene, optionally toluene, and xylenes (often para-xylene, sometimes ortho-xylene). An aromatic complex generally possesses at least one catalytic unit exhibiting at least one of the following functions:
  the isomerization of aromatic compounds containing 8 carbon atoms, denoted A8 compounds, making it possible to convert ortho-xylene, meta-xylene and ethylbenzene into para-xylene;
  transalkylation, making it possible to produce xylenes from a mixture of toluene (and optionally of benzene) and of A9+ compounds, such as trimethylbenzenes and tetramethylbenzenes; and
  the disproportionation of toluene, which makes it possible to produce benzene and xylenes.

The aromatic loop makes it possible to produce high-purity para-xylene by separation by adsorption or by crystallization, an operation which is well known from the prior art. This "C8 aromatic loop" includes a step of removal of the heavy compounds (i.e., C9+ compounds) in a distillation column known as a "xylenes column". The top stream from this column, which contains the C8 aromatic isomers (i.e., A8 isomers), is subsequently sent to the process for separation of the para-xylene which is, very generally, a process for separation by simulated moving bed (SMB) adsorption, to produce an extract and a raffinate, or a crystallization process, in which a para-xylene fraction is isolated from the remainder of the constituents of the mixture in the form of crystals.

The extract, which contains the para-xylene, is subsequently distilled in order to obtain high-purity para-xylene. The raffinate, which is rich in meta-xylene, ortho-xylene and ethylbenzene, is treated in a catalytic isomerization unit which restores a mixture of C8 aromatics in which the proportion of the xylenes (ortho-, meta-, para-xylenes) is virtually at thermodynamic equilibrium and the amount of ethylbenzene is reduced. This mixture is again sent to the "xylenes column" with the fresh feedstock.

The aromatic complexes producing benzene and para-xylene are very predominantly fed by feedstocks derived from oil or natural gas. These complexes do not make it possible to produce biobased aromatics. Another challenge is to upgrade the carbon in the form of CO and $CO_2$, and in particular the biobased carbon, to high-value-added compounds. The object of the present invention is to overcome these drawbacks.

SUMMARY OF THE INVENTION

In the context described above, a first object of the present description is to overcome the problems of the prior art and to provide a device and a process for the production of aromatics for the petrochemical industry making it possible, when the aromatic compounds are produced by pyrolysis of hydrocarbon compounds, to convert (for example all) the CO and $CO_2$, by-products of the pyrolysis section, into additional aromatic compounds and paraffins. The $CO_2$ originating from the combustion of the coke present on the catalyst of the pyrolysis process may also advantageously be converted into aromatic compounds.

The invention is based on the conversion of the carbon monoxide, i.e., CO, and of the carbon dioxide, i.e. $CO_2$, into paraffins and into aromatic compounds which are introduced into the aromatic complex, and notably on the provision of one or more units that make it possible to convert the CO and the $CO_2$ into ethanol which is converted into aromatic compounds by recycling to the pyrolysis unit. The aromatic compounds derived from the conversion of ethanol are treated within the aromatic loop as a mixture with the aromatic compounds directly derived from the pyrolysis of the hydrocarbon compounds.

Specifically, the object of the present invention may consist of adding a reverse water gas shift (RWGS) unit in order to at least partially convert the $CO_2$ into CO and to thus obtain a CO-enriched gas, followed by a unit for fermentation of the CO into ethanol. The $CO_2$ present at the outlet of the fermentation unit is recycled to the inlet of the reverse water gas shift unit, thus enabling the complete conversion of the $CO_2$. The ethanol produced by the fermentation of the CO is converted into aromatic compounds by recycling to the pyrolysis unit.

According to a first aspect, the aforementioned objects, and also other advantages, are obtained by a device for converting a first hydrocarbon feedstock comprising aromatic compounds, comprising:
  a fractionation train suitable for extracting at least one benzene-comprising cut, one toluene-comprising cut and one cut comprising xylenes and ethylbenzene from the first hydrocarbon feedstock;
  a unit for the separation of the xylenes suitable for treating the cut comprising xylenes and ethylbenzene and producing an extract comprising para-xylene and a raffinate comprising ortho-xylene, meta-xylene and ethylbenzene;

an isomerization unit suitable for treating the raffinate and producing an isomerate enriched in para-xylene which is sent to the fractionation train;

a pyrolysis unit suitable for treating a second hydrocarbon feedstock, producing at least one pyrolysis effluent comprising hydrocarbon compounds having 6 to 10 carbon atoms feeding, at least partially, the first hydrocarbon feedstock, and producing a pyrolysis gas comprising at least CO, $CO_2$ and $H_2$;

a reverse water gas shift RWGS reaction section suitable for treating the pyrolysis gas and producing an RWGS gas enriched in CO and in water;

a fermentation reaction section suitable for treating the RWGS gas enriched in CO and in water, producing ethanol and recycling the ethanol to the inlet of the pyrolysis unit.

One of the advantages of the invention is notably to be able to send, without a separation step, the effluent resulting from the RWGS (for example in its entirety) containing a mixture consisting of CO, $CO_2$, $H_2O$ and $H_2$ directly into the fermentation reaction section in order to produce ethanol. Moreover, the ethanol thus produced may be upgraded directly by recycling to the pyrolysis unit.

According to one or more embodiments, the fermentation reaction section is suitable for recycling $CO_2$ present at the fermentation outlet to the inlet of the RWGS reaction section.

According to one or more embodiments, the device further comprises a makeup line for providing a supply of $H_2$ to the pyrolysis gas.

According to one or more embodiments, the fractionation train is suitable for extracting a C9-C10 monoaromatics cut from the first hydrocarbon feedstock.

According to one or more embodiments, the device additionally comprises a transalkylation unit suitable for treating the C9-C10 monoaromatics cut with the toluene-comprising cut and producing xylenes which are sent to the fractionation train.

According to one or more embodiments, the device additionally comprises a selective hydrogenolysis unit suitable for:

treating the C9-C10 monoaromatics cut; and producing a hydrogenolysis effluent enriched in methyl-substituted aromatic compounds which is sent to the transalkylation unit.

According to one or more embodiments, the device further comprises a disproportionation unit suitable for treating, at least in part, the toluene-comprising cut and producing a xylene-enriched cut which is recycled to the isomerization unit.

According to a second aspect, the abovementioned objects, and also other advantages, are obtained by a process for converting a first hydrocarbon feedstock comprising aromatic compounds, comprising the following steps:

fractionating the first hydrocarbon feedstock in a fractionation train in order to extract at least one benzene-comprising cut, one toluene-comprising cut and one cut comprising xylenes and ethylbenzene;

separating the cut comprising xylenes and ethylbenzene in a unit for the separation of the xylenes and producing an extract comprising para-xylene and a raffinate comprising ortho-xylene, meta-xylene and ethylbenzene;

isomerizing the raffinate in an isomerization unit and producing an isomerate enriched in para-xylene;

sending the isomerate enriched in para-xylene to the fractionation train;

treating a second hydrocarbon feedstock in a pyrolysis unit in order to produce at least one pyrolysis effluent comprising hydrocarbon compounds having 6 to 10 carbon atoms feeding, at least partially, the first hydrocarbon feedstock and producing a pyrolysis gas comprising at least CO, $CO_2$ and $H_2$;

treating the pyrolysis gas in an RWGS reaction section in order to produce an RWGS gas enriched in CO and in water;

treating, at least in part, the RWGS gas enriched in CO and in water in a fermentation reaction section in order to produce ethanol; and recycling the ethanol to the inlet of the pyrolysis unit.

According to one or more embodiments, the process comprises a step of recycling $CO_2$ present at the fermentation outlet to the inlet of the RWGS reaction section.

According to one or more embodiments, the process further comprises providing a supply of $H_2$ to the pyrolysis gas by means of a makeup line.

According to one or more embodiments, the pyrolysis unit comprises at least one reactor used under at least one of the following operating conditions:

absolute pressure of between 0.1 and 0.5 MPa and HSV of between 0.01 and 10 $h^{-1}$, preferably between 0.01 and 5 $h^{-1}$, and very preferably between 0.1 and 3 $h^{-1}$ (the HSV is the ratio of the volume flow rate of feedstock to the volume of catalyst used);

temperature of between 400° C. and 1000° C., preferably between 400° C. and 650° C., preferably between 450° C. and 600° C. and preferably between 450° C. and 590° C.;

zeolite catalyst comprising and preferably constituted of at least one zeolite chosen from ZSM-5, ferrierite, zeolite beta, zeolite Y, mordenite, ZSM-23, ZSM-57, EU-1 and ZSM-11, and preferably the catalyst is a catalyst comprising only ZSM-5.

According to one or more embodiments, the RWGS reaction section comprises at least one reactor used under at least one of the following operating conditions:

temperature of between 400° C. and 800° C., preferentially of between 500° C. and 800° C. and more preferentially still of between 650° C. and 750° C.;

pressure of between 0.1 and 10 MPa, preferentially of between 0.1 and 5 MPa and more preferentially of between 0.1 and 2.5 MPa;

space velocity of the gas at the inlet of the reactor of between 5000 and 20 000 $mL/g_{cata}/h$;

catalysts based on iron or alkali metals (for example potassium).

According to one or more embodiments, the fermentation reaction section comprises at least one reactor used under at least one of the following operating conditions:

presence of a microorganism capable of metabolizing the CO and/or the $CO_2/H_2$ pair to produce ethanol;

pH of between 3 and 9;

growth temperature of between 20° C. and 80° C.;

redox potential of greater than −450 mV;

pressure of between 0.1 and 0.4 MPa.

According to one or more embodiments, the isomerization unit comprises a gas-phase isomerization zone and/or a liquid-phase isomerization zone, in which the gas-phase isomerization zone is used under at least one of the following operating conditions:

temperature of greater than 300° C.;

pressure of less than 4.0 MPa;

hourly space velocity of less than 10 h$^{-1}$;

hydrogen-to-hydrocarbon molar ratio of less than 10;

in the presence of a catalyst comprising at least one zeolite exhibiting channels, the opening of which is defined by a ring having 10 or 12 oxygen atoms, and at least one metal from group VIII with a content of between 0.1% and 0.3% by weight, limits included, and in which the liquid-phase isomerization zone is used under at least one of the following operating conditions:

temperature of less than 300° C.;

pressure of less than 4 MPa;

hourly space velocity of less than 10 h$^{-1}$;

in the presence of a catalyst comprising at least one zeolite exhibiting channels, the opening of which is defined by a ring having 10 or 12 oxygen atoms.

Embodiments according to the first aspect and the second aspect, and also other characteristics and advantages of the devices and processes according to the abovementioned aspects, will become apparent on reading the description which will follow, which is given solely by way of illustration and without limitation, and with reference to the following drawing.

BRIEF DESCRIPTION OF THE DRAWINGS

FIGURE represents a diagrammatic view of a process according to the present invention which makes it possible to increase the production of aromatic compounds.

DESCRIPTION OF THE EMBODIMENTS

Embodiments of the device according to the first aspect and of the process according to the second aspect will now be described in detail. In the following detailed description, numerous specific details are disclosed in order to provide a deeper understanding of the device. However, it will be apparent to a person skilled in the art that the device can be implemented without these specific details. In other cases, well-known characteristics have not been described in detail in order to avoid unnecessarily complicating the description.

In the present patent application, the term "to comprise" is synonymous with (means the same thing as) "to include" and "to contain", and is inclusive or open and does not exclude other elements which are not stated. It is understood that the term "to comprise" includes the exclusive and closed term "to consist". Moreover, in the present description, an effluent comprising essentially or solely compounds A corresponds to an effluent comprising at least 80% or 90% by weight, preferably at least 95% by weight, very preferably at least 99% by weight, of compounds A.

The present invention may be defined as a device and a process comprising a sequence of unitary operations which make it possible to produce para-xylene and benzene.

The device and the process according to the invention are characterized in that they comprise and use the catalytic units and the separation units which are known to a person skilled in the art for producing benzene and para-xylene, which units are commonly encountered in aromatic complexes.

One of the characteristics of the present invention can be summarized as the use of CO and CO$_2$, by-products of a unit for the pyrolysis of hydrocarbon compounds, for increasing the production of aromatic compounds.

Advantageously, the combination of a reaction section for the conversion of the CO$_2$ into CO by RWGS reaction, of a reaction section for the fermentation into ethanol of the CO present in the gas enriched in CO and in water leaving the RWGS unit, and of the recycling of the ethanol to the inlet of the pyrolysis unit makes it possible to significantly increase the amount of aromatics produced by pyrolysis of hydrocarbon compounds and to potentially upgrade all of the CO and CO$_2$ by-products of the pyrolysis unit.

With reference to FIG. 1, according to one or more embodiments, the device for conversion of aromatic compounds comprises:

an optional feedstock separation unit 1 for separating a first hydrocarbon feedstock 2 of the aromatic complex into a hydrocarbon cut having 7 or less carbon atoms (C7−) and an aromatic cut having 8 or more carbon atoms (A8+);

an optional aromatics extraction unit 3 between the feedstock separation unit 1 and a fractionation train 4-7 in order to separate the aliphatic compounds from the benzene and the toluene of the C7− cut of the feedstock of the complex;

the fractionation train 4-7 downstream of the optional aromatics extraction unit 3 making it possible to extract the benzene, the toluene and the xylenes from the other aromatics;

an optional transalkylation unit 8 which converts toluene (and optionally benzene) and methylalkylbenzenes, such as trimethylbenzenes, into xylenes—advantageously, this unit can also treat tetramethylbenzenes;

an optional selective hydrogenolysis unit 9 suitable for treating a cut comprising aromatic compounds having 9 and 10 carbon atoms and producing a hydrogenolysis effluent enriched in methyl-substituted aromatic compounds;

an optional separation unit (not shown) for separating the hydrogenolysis effluent positioned (e.g., directly) downstream of the selective hydrogenolysis unit 9, for producing a plurality of liquid effluent cuts;

a xylene separation unit 10 (e.g., of the type of crystallization or simulated moving bed using a molecular sieve and a desorbent, such as toluene) making it possible to isolate the para-xylene from the xylenes and the ethylbenzene;

a unit 11 for isomerization of the raffinate obtained as effluent from the xylene separation unit 10, in order to convert in particular the ortho-xylene, the meta-xylene and the ethylbenzene into para-xylene;

an optional stabilization column 12 which makes it possible in particular to remove the more volatile entities (e.g., C5− entities) from the aromatic complex, in particular effluents from the transalkylation unit 8 and/or the isomerization unit 11;

a pyrolysis unit 13, preferably a catalytic pyrolysis unit, for treating a second hydrocarbon feedstock 30, producing at least one pyrolysis effluent 31 feeding, at least partially, the first hydrocarbon feedstock 2 of the aromatic complex, a pyrolysis gas 32 comprising CO, CO$_2$ and H$_2$, and by-products 33 (composed predominantly of middle distillates which, after hydrotreating and/or hydrocracking, will be able to be upgraded in the form of jet fuel, diesel fuel or marine fuel);

a first optional makeup line 34 for providing a supply of H$_2$ and adjusting the H$_2$/CO ratio of the pyrolysis gas 32;

an RWGS reaction section 50 for treating the pyrolysis gas 32 originating from the pyrolysis unit 13, and for producing an RWGS gas 51 enriched in CO and in water (and thus depleted in CO$_2$ and in H$_2$) compared to the pyrolysis gas 32;

a fermentation reaction section 52 for treating the RWGS gas 51 enriched in CO and in water and for producing a fermentation effluent 53 enriched in ethanol compared to the RWGS gas 51;

a line 35 for recycling the ethanol produced in the fermentation reaction section 52 to the pyrolysis unit 13.

With reference to FIG. 1, the feedstock separation unit 1 treats the first hydrocarbon feedstock 2 of the aromatic complex in order to separate a top cut 16 comprising (e.g., essentially) compounds having 7 or less carbon atoms (C7−), containing in particular benzene and toluene, and a bottom cut 17 comprising (e.g., essentially) aromatics having 8 or more carbon atoms (A8+) which is sent to the xylene column 6. According to one or more embodiments, the feedstock separation unit 1 also separates a first toluene cut 18 comprising at least 90% by weight, preferably at least 95% by weight, very preferably at least 99% by weight, of toluene. According to one or more embodiments, the first toluene cut 18 is sent to the first column 4 for the distillation of aromatic compounds, also referred to as benzene column, and/or to the second column 5 for the distillation of aromatic compounds, also referred to as toluene column.

According to one or more embodiments, the first hydrocarbon feedstock 2 is a hydrocarbon cut containing predominantly (i.e., >50% by weight) molecules of which the carbon number extends from 6 to 10 carbon atoms. This feedstock can also contain molecules having more than 10 carbon atoms and/or molecules having 5 carbon atoms.

The first hydrocarbon feedstock 2 of the aromatic complex is rich in aromatics (e.g. >50% by weight) and contains preferably at least 20% by weight of benzene, preferentially at least 30% by weight, very preferably at least 40% by weight, of benzene. The first hydrocarbon feedstock 2 can be produced by catalytic reforming of a naphtha or be a product of a cracking (e.g., steam cracking, catalytic cracking) unit or any other means for producing alkylaromatics.

According to one or more embodiments, the first hydrocarbon feedstock 2 is at least partially, or even completely, biobased. According to one or more embodiments, the first hydrocarbon feedstock 2 originates (essentially) from a lignocellulosic biomass conversion process. For example, an effluent produced by conversion of lignocellulosic biomass can be treated to meet the required specifications of the first hydrocarbon feedstock 2 in order to exhibit contents of sulfur-based, nitrogen-based and oxygen-based elements which are compatible with an aromatic complex.

According to one or more embodiments, the first hydrocarbon feedstock 2 of the aromatic complex comprises at least 25% by weight, preferably at least 30% by weight, very preferably at least 35% by weight, of pyrolysis effluent 31 originating from the pyrolysis unit 13 relative to the total weight of the feedstock, the balance comprising (preferably consisting of) a non-biobased mixture of aromatic and paraffinic compounds (originating for example from a catalytic reforming unit). According to one or more embodiments, the first hydrocarbon feedstock 2 of the aromatic complex comprises at least 80% by weight, preferably at least 90% by weight, very preferably at least 95% by weight, of pyrolysis effluent 31 originating from the pyrolysis unit 13. According to one or more embodiments, the first hydrocarbon feedstock 2 of the aromatic complex consists of the pyrolysis effluent 31 originating from the pyrolysis unit 13.

According to one or more embodiments, the first hydrocarbon feedstock 2 comprises less than 10 ppm by weight, preferably less than 5 ppm by weight, very preferably less than 1 ppm by weight, of elemental nitrogen, and/or less than 10 ppm by weight, preferably less than 5 ppm by weight, very preferably less than 1 ppm by weight, of elemental sulfur, and/or less than 100 ppm by weight, preferably less than 50 ppm by weight, very preferably less than 10 ppm by weight, of elemental oxygen.

The top cut 16 from the feedstock separation unit 1, optionally mixed with the bottom product (benzene and toluene) from the stabilization column 12, which will be defined below, is sent to the aromatics extraction unit 3 in order to extract an effluent 19 comprising C6-C7 aliphatic entities, which is exported as co-product from the aromatic complex. The aromatic cut 20 (essentially benzene and toluene), referred to as extract from the aromatics extraction unit 3, optionally mixed with the heavy fraction 21 from the transalkylation unit 8, which will be defined below, is sent to the benzene column 4. According to one or more embodiments, the aromatic cut 20 is a C6-C7 (e.g., essentially) aromatic hydrocarbon feedstock (A6-A7).

According to one or more embodiments, the fractionation train comprises the columns 4, 5, 6 and 7 for the distillation of aromatic compounds, making it possible to separate the following five cuts:

a cut 22 comprising (e.g., essentially) benzene;
a cut 23 comprising (e.g., essentially) toluene;
a cut 24 comprising (e.g., essentially) xylenes and ethylbenzene;
a cut 25 comprising (e.g., essentially) aromatic compounds having 9 and 10 carbon atoms;
a cut 26 comprising (e.g., essentially) aromatic compounds, the most volatile entities of which are aromatics having 10 carbon atoms.

The benzene column 4 is suitable for: treating the aromatic cut 20, which is a C6-C10 (e.g., essentially) aromatic hydrocarbon feedstock (A6+); producing, at the top, the cut 22 comprising benzene, which may be one of the desired products at the outlet of the aromatic complex; and producing, at the bottom, a C7-C10 (e.g., essentially) aromatic effluent 27 (A7+).

The toluene column 5 is suitable for: treating the C7-C10 aromatic effluent 27 (A7+), which is the bottom product from the benzene column 4; producing, at the top, the toluene-comprising cut 23, which is sent to the transalkylation unit 8; and producing, at the bottom, a C8-C10 (e.g., essentially) aromatic effluent 28 (A8+).

The third column 6 for the distillation of aromatic compounds, also referred to as xylene column, is suitable for: treating the aromatic cut 17 having 8 or more carbon atoms (A8+) of the feedstock of the aromatic complex and optionally the bottom effluent 28 from the toluene column; producing, at the top, the cut 24 comprising xylenes and ethylbenzene, which is sent to the xylene separation unit 10; and producing, at the bottom, an effluent 29 (e.g., essentially) comprising C9-C10 aromatics (A9+).

The fourth column 7 for the distillation of aromatic compounds, also referred to as heavy aromatics column, is optional and is suitable for: treating the bottom effluent 29 from the xylene column; producing, at the top, the fraction 25 comprising C9-C10 monoaromatics; and producing, at the bottom, the cut 26 comprising (e.g., essentially) aromatic compounds, the most volatile entities of which are aromatics having 10 carbon atoms (A10+). Preferably, the bottom cut 26 comprises C11+ compounds.

In the transalkylation unit 8, the fraction 25 comprising C9-C10 monoaromatics (and/or the hydrogenolysis effluent enriched in methyl-substituted aromatic compounds described below) is mixed with the toluene-comprising cut 23 originating from the top of the toluene column 5 and feeds the reaction section of the transalkylation unit 8 to produce xylenes by transalkylation of aromatics with a deficit of methyl groups (toluene) and aromatics with an excess of methyl groups (e.g., tri- and tetramethylbenzenes). According to one or more embodiments, the transalkylation unit 8 is fed with benzene (line not represented in FIG. 1), for example when an excess of methyl groups is observed, for the production of para-xylene. According to one or more embodiments, the transalkylation unit 8 directly treats the bottom effluent 29 from the xylene column.

According to one or more embodiments, the transalkylation unit 8 comprises at least one first transalkylation reactor suitable for being used under at least one of the following operating conditions:

- temperature of between 200° C. and 600° C., preferentially of between 350° C. and 550° C. and more preferentially still of between 380° C. and 500° C.;
- pressure of between 2 and 10 MPa, preferentially of between 2 and 6 MPa and more preferentially of between 2 and 4 MPa;
- WWH of between 0.5 and 5 $h^{-1}$, preferentially of between 1 and 4 $h^{-1}$, and more preferentially of between 2 and 3 $h^{-1}$.

According to one or more embodiments, the first transalkylation reactor is operated in the presence of a catalyst comprising zeolite, for example ZSM-5. According to one or more embodiments, the second transalkylation reactor is of fixed bed type.

According to one or more embodiments, the effluents from the reaction section of the transalkylation unit 8 are separated in a first separation column (not represented) downstream of said reaction section of the transalkylation unit 8. A cut 38 comprising at least a portion of the benzene and the more volatile entities (C6−) is extracted at the top of the first separation column and is sent to an optional stabilization column 12, making it possible in particular to remove the more volatile entities (e.g., C5−) from the aromatic complex. The heavy fraction 21 of the effluents from the first separation column comprising (e.g., essentially) aromatics having at least 7 carbon atoms (A7+) is optionally recycled to the fractionation train 4-7, for example to the benzene column 4.

The cut 24 comprising xylenes and ethylbenzene is treated in the xylene separation unit 10 to produce a fraction or an extract 39, comprising para-xylene, and a raffinate 40. The extract 39 can be subsequently distilled (e.g., if separation by SMB adsorption), for example by means of an extract column and then of an additional toluene column (which are not shown) in the case where toluene is used as desorbent, in order to obtain high-purity para-xylene exported as main product. The raffinate 40 from the xylene separation unit 10 comprises (e.g., essentially) ortho-xylene, meta-xylene and ethylbenzene and feeds the isomerization unit 11.

According to one or more embodiments, the xylene separation unit 10 also separates a second toluene cut 41 comprising at least 90% by weight, preferably at least 95% by weight, very preferably at least 99% by weight, of toluene. The toluene cut 41 can, for example, be a portion of the toluene used as desorbent when the xylene separation unit 10 comprises a "simulated moving bed" adsorption unit. According to one or more embodiments, the second toluene cut 41 is sent to the transalkylation unit 8.

In the isomerization reaction section of the isomerization unit 11, the isomers of the para-xylene are isomerized, whereas the ethylbenzene can be: isomerized to give a mixture of C8 aromatics, for example if it is desired to produce mainly para-xylene; and/or dealkylated to produce benzene, for example if it is desired to produce both para-xylene and benzene.

According to one or more embodiments, the effluents from the isomerization reaction section are sent to a second separation column (not represented) to produce, at the bottom, an isomerate 42 enriched in para-xylene, which is preferably recycled to the xylene column 6; and to produce, at the top, a hydrocarbon cut 43 comprising compounds having 7 or less carbon atoms (C7−) which is sent to the optional stabilization column 12, for example with the cut 38 comprising at least a portion of the benzene and the more volatile entities.

According to one or more embodiments, the isomerization unit 11 comprises a first isomerization zone working in the liquid phase and/or a second isomerization zone working in the gas phase. According to one or more embodiments, the isomerization unit 11 comprises a first isomerization zone working in the liquid phase and a second isomerization zone working in the gas phase. According to one or more embodiments, a first portion of the raffinate 40 is sent to the liquid-phase isomerization unit, in order to obtain a first isomerate feeding directly and at least in part the separation unit 10, and a second portion of the raffinate 40 is sent to the gas-phase isomerization unit, in order to obtain an isomerate which is sent to the xylene column 6.

According to one or more embodiments, the gas-phase isomerization zone is suitable for being used under at least one of the following operating conditions:

- temperature of greater than 300° C., preferably from 350° C. to 480° C.;
- pressure of less than 4.0 MPa, and preferably from 0.5 to 2.0 MPa;
- hourly space velocity of less than 10 $h^{-1}$ (10 litres per litre per hour), preferably between 0.5 $h^{-1}$ and 6 $h^{-1}$;
- hydrogen-to-hydrocarbon molar ratio of less than 10, and preferably of between 3 and 6;
- in the presence of a catalyst comprising at least one zeolite exhibiting channels, the opening of which is defined by a ring having 10 or 12 oxygen atoms (10 MR or 12 MR), and at least one metal from group VIII with a content of between 0.1% and 0.3% by weight (reduced form), limits included.

According to one or more embodiments, the liquid-phase isomerization zone is suitable for being used under at least one of the following operating conditions:

- temperature of less than 300° C., preferably 200° C. to 260° C.;
- pressure of less than 4 MPa, preferably 2 to 3 MPa;
- hourly space velocity (HSV) of less than 10 $h^{-1}$ (10 litres per litre per hour), preferably of between 2 and 4 $h^{-1}$;
- in the presence of a catalyst comprising at least one zeolite exhibiting channels, the opening of which is defined by a ring having 10 or 12 oxygen atoms (10 MR or 12 MR), preferentially a catalyst comprising at least one zeolite exhibiting channels, the opening of which is defined by a ring having 10 oxygen atoms (10 MR), and more preferably still a catalyst comprising a zeolite of ZSM-5 type.

The term HSV corresponds to the volume of hydrocarbon feedstock injected hourly, with respect to the volume of catalyst charged.

According to one or more embodiments, the optional stabilization column 12 produces: at the bottom, a stabilized cut 44 comprising (e.g., essentially) benzene and toluene, which is optionally recycled at the inlet of the feedstock separation unit 1 and/or of the aromatics extraction unit 3;

and, at the top, a cut 45 of more volatile entities (e.g., C5−), which is removed from the aromatic complex.

According to one or more embodiments, the selective hydrogenolysis unit 9 is suitable for:
- treating the monoaromatics 25 having between 9 and 10 carbon atoms; and
- producing a hydrogenolysis effluent 46 enriched in methyl-substituted aromatic compounds.

Specifically, the selective hydrogenolysis unit 9 can be suitable for treating the aromatics 25 having between 9 and 10 carbon atoms by converting one or more alkyl groups having at least two carbon atoms (ethyl, propyl, butyl, isopropyl, etc. groups) attached to a benzene ring into one or more methyl groups, that is to say groups formed of a single $CH_3$ group. The major advantage of the selective hydrogenolysis unit 9 is that of increasing the content of $CH_3$ groups and lowering the content of ethyl, propyl, butyl, isopropyl, etc. groups in the feedstock of the isomerization unit 11, in order to increase the rate of production of xylenes, and in particular of para-xylene, in said isomerization unit 11.

According to one or more embodiments, the selective hydrogenolysis unit 9 comprises at least one hydrogenolysis reactor suitable for being used under at least one of the following operating conditions:
- temperature of between 300° C. and 550° C., preferentially of between 350° C. and 500° C. and more preferentially still of between 370° C. and 450° C.;
- pressure of between 0.1 and 3 MPa, preferentially of between 0.2 and 2 MPa and more preferentially of between 0.2 and 1 MPa;
- $H_2$/HC (hydrocarbon feedstock) molar ratio of between 1 and 10 and preferentially of between 1.5 and 6;
- WWH of between 0.1 and 50 $h^{-1}$ (e.g., 0.5-50 $h^{-1}$), preferentially of between 0.5 and 30 $h^{-1}$ (e.g., 1-30 $h^{-1}$) and more preferentially of between 1 and 20 $h^{-1}$ (e.g., 2-20 $h^{-1}$, 5-20 $h^{-1}$).

According to one or more embodiments, the hydrogenolysis reactor is operated in the presence of a catalyst comprising at least one metal from group VIII of the Periodic Table, preferably nickel and/or cobalt, deposited on a porous support comprising at least one crystalline or noncrystalline refractory oxide having structured or unstructured porosity. According to one or more embodiments, the metal from group VIII is nickel. The presence of a promoter (group VIB VIIB VIII IB or IIB) is also possible. The catalyst is supported on a refractory oxide (e.g., alumina or silica), optionally treated with a base in order to neutralize it.

According to one or more embodiments, the hydrogenolysis reactor is of fixed bed type and the catalyst support is in the form of extrudates. According to one or more embodiments, the hydrogenolysis reactor is of moving bed type, and the catalyst support is in the form of approximately spherical beads. A moving bed can be defined as being a gravity flow bed, such as those encountered in the catalytic reforming of petroleums.

According to one or more embodiments, the second hydrocarbon feedstock 30 is a mixture of hydrocarbon compounds having a content of elemental oxygen at least greater than 1% by weight, preferentially 3% by weight, very preferentially 5% by weight, relative to the total weight of said feedstock. According to one or more embodiments, the second hydrocarbon feedstock 30 comprises or consists of lignocellulosic biomass or one or more constituents of lignocellulosic biomass chosen from the group formed by cellulose, hemicellulose and lignin.

Lignocellulosic biomass may consist of wood, agricultural waste or plant waste. Other non-limiting examples of lignocellulosic biomass material are farm residues (straw, maize stover, etc.), forestry residues (products from first thinning), forestry products, dedicated crops (short-rotation coppice), residues from the food processing industry, organic household wastes, wastes from woodworking plants, waste wood from the building industry, recycled or non-recycled paper.

Lignocellulosic biomass may also come from by-products of the papermaking industry such as Kraft lignin, or black liquors resulting from the manufacture of paper pulp.

The lignocellulosic biomass may advantageously undergo at least one pretreatment step before it is introduced into the process according to the invention. Preferably, the biomass is ground and dried, until the desired particle size is obtained. A feedstock exhibiting a particle diameter of between 0.3 and 0.5 mm can advantageously be obtained. Typically, the size of the particles of the lignocellulosic biomass to be pyrolyzed is a particle size sufficient to pass through a 1 mm screen up to a particle size sufficient to pass through a 30 mm screen.

According to one or more embodiments, when the second hydrocarbon feedstock 30 is solid (e.g. biomass-type feedstock), the second hydrocarbon feedstock 30 to be pyrolyzed is advantageously charged to a pneumatic entrainment or transportation compartment so as to be entrained into a pyrolysis reactor by an entraining fluid. Preferably, the entraining fluid used is gaseous nitrogen. However, it is also envisaged that other non-oxidizing entraining fluids can be used. Preferably, a portion of the pyrolysis gas produced during the process may be recycled and used as entraining fluid. Said pyrolysis gas mainly consists of a noncondensable gaseous effluent, comprising at least carbon monoxide (CO) and carbon dioxide ($CO_2$), and also advantageously comprising light olefins comprising from 2 to 4 carbon atoms. In this way, the costs of carrying out the pyrolysis can be considerably reduced. The second hydrocarbon feedstock 30 may be charged to a feed hopper or another device which makes it possible to convey said feedstock into the entrainment compartment in an appropriate amount. In this way, a constant amount of feedstock is delivered to the entrainment compartment.

The entraining fluid advantageously transports the second hydrocarbon feedstock 30 from the entrainment compartment into the pyrolysis reactor through a feed tube.

Typically, the feed tube is cooled to maintain the temperature of the second hydrocarbon feedstock 30 at a required level before it enters the pyrolysis reactor. The feed tube can be cooled by jacketing the tube, typically with an air-cooled or liquid-cooled jacket. However, it is also envisaged for the feed tube not to be cooled.

According to one or more embodiments, the pyrolysis unit 13 comprises at least one pyrolysis reactor (e.g. fluidized bed pyrolysis reactor) suitable for being used under at least one of the operating conditions listed below.

According to one or more embodiments, the pyrolysis step is carried out at a temperature between 400° C. and 1000° C., preferably between 400° C. and 650° C., preferably between 450° C. and 600° C. and preferably between 450° C. and 590° C. In particular, the use of hot regenerated catalyst originating from a catalyst regeneration step may make it possible to provide temperature ranges of the reactor.

The pyrolysis step is also advantageously carried out at an absolute pressure of between 0.1 and 0.5 MPa and at an HSV of between 0.01 and 10 $h^{-1}$, preferably between 0.01 and 5 h⁻¹, and very preferably between 0.1 and 3 h⁻¹. The HSV is the ratio of the volume flow rate of feedstock to the volume of catalyst used.

According to one or more embodiments, the pyrolysis step is catalytic and is carried out in the presence of a catalyst. Preferably, said step operates in the presence of a zeolite catalyst comprising and preferably consisting of at least one zeolite chosen from ZSM-5, ferrierite, zeolite beta, zeolite Y, mordenite, ZSM-23, ZSM-57, EU-1 and ZSM-11, and preferably the catalyst is a catalyst comprising only ZSM-5. The zeolite used in the catalyst employed in the catalytic pyrolysis step may advantageously be doped, preferably with a metal chosen from iron, gallium, zinc and lanthanum.

Under these conditions, the second hydrocarbon feedstock 30 will firstly undergo, in the reactor, a rapid pyrolysis on coming into contact with the hot catalyst originating from the regenerator, which in this step acts as heat carrier. The gases resulting from this pyrolysis will subsequently react over the catalyst, which this time performs its role of catalyst making it possible to catalyse the reactions producing the desired chemical intermediates.

In the pyrolysis unit 13, the second hydrocarbon feedstock 30 is in particular converted, at least partially, into a pyrolysis effluent 31 comprising hydrocarbon compounds, the carbon number of which extends from 6 to 10 carbon atoms, a pyrolysis gas 32 and by-products 33. The pyrolysis effluent 31 feeds the first hydrocarbon feedstock 2 of the aromatic complex. The pyrolysis unit 13 also produces a pyrolysis gas 32 comprising CO, $CO_2$ and $H_2$, and by-products 33.

The products obtained at the end of the pyrolysis step are advantageously recovered in the form of a gaseous effluent comprising BTX.

Said gaseous effluent comprising the products obtained at the end of the pyrolysis step is then advantageously sent to a fractionation section, so as to separate at least the following cuts:

a gaseous fraction of noncondensable gases, comprising at least carbon monoxide (CO) and carbon dioxide ($CO_2$), a liquid cut referred to as BTX, comprising hydrocarbon compounds, the carbon number of which extends from 6 to 10 carbon atoms, a liquid cut predominantly comprising compounds having a number of carbon atoms greater than 9, i.e. at least 50% by weight of C9+ compounds, and water.

Said gaseous fraction of noncondensable gases may also advantageously comprise light olefins comprising from 2 to 4 carbon atoms.

The coked catalyst and also the unconverted second hydrocarbon feedstock, usually referred to as "char", are advantageously withdrawn from the reactor and preferably sent to a stripper so as to remove the hydrocarbons potentially adsorbed, and thus prevent their combustion in the regenerator, by contacting with at least one gas chosen from steam, an inert gas such as nitrogen for example and a portion of the gaseous fraction of noncondensable gases resulting from the fractionation of the gaseous effluent derived from the pyrolysis step.

Said coked catalyst and the unconverted second hydrocarbon feedstock, which are optionally stripped, are advantageously sent to a regenerator where coke and char are burnt by addition of air or oxygen, thus producing regenerated catalyst and a $CO_2$-rich combustion gas.

According to one or more embodiments, the regenerated catalyst is advantageously recycled in the reactor of the pyrolysis step in order to undergo another cycle.

Advantageously, the pyrolysis step of the process according to the invention enables the production of at least 10% by weight and preferably of at least 15% by weight of aromatics, relative to the total weight of the reaction products obtained, with a selectivity of at least 65% and preferably of at least 70% for BTX.

The process thus comprises at least one pyrolysis step that produces at least one BTX cut (pyrolysis effluent 31) and one gaseous fraction of noncondensable gases (pyrolysis gas 32) comprising at least carbon monoxide and carbon dioxide.

The process also makes it possible to obtain, in addition to the BTX cut, a heavier liquid fraction, which is predominantly aromatic, referred to as "C9+ cut", which may advantageously be upgraded in a process external to the process according to the invention.

Preferably, at least one portion of the gaseous fraction of noncondensable gases is recycled, preferably via a compressor, to the reactor of the pyrolysis step. This gas stream then serves as fluid for entrainment of the feedstock into said reactor. In this case, a purge of said gaseous recycle effluent is preferably carried out, preferably either upstream or downstream of said compressor.

According to one or more embodiments, the pyrolysis effluent 31 is a hydrocarbon cut containing predominantly (i.e., >50% by weight) molecules of which the carbon number extends from 6 to 10 carbon atoms. This pyrolysis effluent 31 can also contain molecules having more than 10 carbon atoms and/or molecules having 5 carbon atoms. The pyrolysis effluent 31 is rich in aromatics (e.g. >50% by weight) and contains preferably at least 20% by weight of benzene, preferentially at least 30% by weight, very preferably at least 40% by weight, of benzene. According to one or more embodiments, the pyrolysis effluent 31 is treated to meet the required specifications of the first hydrocarbon feedstock 2 as described above, in order to exhibit contents of sulfur-based, nitrogen-based and oxygen-based elements which are compatible with an aromatic complex.

According to one or more embodiments, the pyrolysis gas 32 comprises at least one portion of the gaseous fraction of noncondensable gases and preferably comprises, at least in part, the $CO_2$-rich combustion gas. According to one or more embodiments, the pyrolysis gas 32 produced by the pyrolysis unit 13 comprises a mixture containing predominantly (e.g., comprising at least 50% by weight) hydrogen, CO and $CO_2$. According to one or more embodiments, the pyrolysis gas 32 comprises at least 20% by weight of CO, preferably at least 30% by weight of CO, very preferably at least 40% by weight of CO (e.g., at least 50% by weight of CO). According to one or more embodiments, the pyrolysis gas 32 comprises at least 0.2% by weight of $H_2$, preferably at least 0.5% by weight of $H_2$, very preferably at least 0.8% by weight of $H_2$. According to one or more embodiments, the pyrolysis gas 32, at the outlet of the pyrolysis unit 13, contains at least 20% by weight of $CO_2$. According to one or more embodiments, the pyrolysis gas 32, at the outlet of the pyrolysis unit 13, contains around 30% (e.g. ±10% by weight) by weight of $CO_2$. According to one or more embodiments, the pyrolysis gas 32 contains methane, ethylene and propylene (e.g., less than 10% by weight) and also ethane, propane and water (e.g., less than 3% by weight).

According to one or more embodiments, the by-products 33 comprise the C9+ fraction mainly consisting of di- and triaromatics which are more or less alkylated. This fraction can be upgraded directly as bunker fuel, for example, or can undergo a hydrotreating and/or hydrocracking in order to improve its properties and to upgrade it to jet fuel or to diesel fuel.

According to one or more embodiments, a supply of $H_2$ fed by the optional makeup line 34 is added to the pyrolysis gas 32 so that the $H_{2/CO2}$ molar ratio of the pyrolysis gas 32 at the inlet of the RWGS reaction section 50 is between 1 and 10, preferably between 1 and 8, very preferably between 1 and 5. The hydrogen content of the pyrolysis gas 32 is preferably modified by addition of hydrogen, so as to at least achieve the stoichiometry of the RWGS reaction: $CO_2+H_2 \rightarrow CO+H_2O$.

In the RWGS reaction section 50, the pyrolysis gas 32 optionally enriched by a supply of $H_2$ is converted at least partially into an RWGS gas 51 enriched in CO and in water (and thus depleted in $CO_2$ and in $H_2$). Specifically, the RWGS reaction corresponds to the reaction of the $CO_2$ and $H_2$ to form CO and water.

The RWGS reaction is well known to those skilled in the art; see for example Journal of $CO_2$ Utilization, vol. 21 (2017) p. 423-428. According to one or more embodiments, the RWGS reaction section 50 comprises at least one reactor used under at least one of the following operating conditions:
  temperature of between 400° C. and 800° C., preferentially of between 500° C. and 800° C. and more preferentially still of between 650° C. and 750° C.;
  pressure of between 0.1 and 10 MPa, preferentially of between 0.1 and 5 MPa and more preferentially of between 0.1 and 2.5 MPa;
  the space velocity of the gas at the inlet of the reactor is between 5000 and 20 000 $mL/g_{cata}/h$.

According to one or more embodiments, the catalyst used in the RWGS reaction section 50 is chosen from the list consisting of catalysts based on iron or on alkali metals (for example potassium). According to one or more embodiments, the catalyst for the RWGS reaction is chosen from the list consisting of catalysts based on $Fe/Al_2O_3$, $Fe$—$Cu/Al_2O_3$, $Fe$—$Cs/Al_2O_3$ and $CuO$—$Fe_2O_3$ doped with Cs. Conversions of 70% by weight of the $CO_2$ are commonly obtained with the operating conditions described above.

According to one or more embodiments, the RWGS reaction section 50 is suitable for operating as a fluid bed or fixed bed.

According to one or more embodiments, the RWGS reaction section 50 is suitable for producing an RWGS gas 51 comprising at least 48% by weight of CO in the mixture of CO, $CO_2$ and $H_2O$, preferably at least 54% by weight of CO, very preferably at least 63% by weight of CO.

According to one or more embodiments, it is not necessary to treat the pyrolysis gas 32 and/or the RWGS gas 51 in an additional dedicated unit.

According to one or more embodiments, the pyrolysis gas 32 and/or the RWGS gas 51 can be purified before being converted into ethanol in the fermentation reaction section 52. The purification of the synthesis gas aims to eliminate the sulfur-containing and nitrogen-containing compounds, halogens, heavy metals and transition metals. The main technologies for the purification of synthesis gases are: adsorption, absorption, catalytic reactions.

The different purification methods are well known to a person skilled in the art; reference may be made, for example, to: Oil & Gas Science and Technology—Rev. IFP Energies nouvelles, Vol. 68 (2013), No. 4, and to Applied Energy, Vol. 237 (2019), p. 227-240.

In accordance with the invention, the process comprises a step of sending (preferably all) the RWGS gas 51 enriched in CO and in water derived from the RWGS step to a fermentation step producing a liquid fermentation stream comprising ethanol.

Preferably, the RWGS gas enriched in CO and in water comprises a carbon monoxide (CO) content of between 48% and 63% by weight of CO, and preferably between 54% and 63% by weight, the percentages being expressed as weight percentages relative to the total weight of said RWGS gas.

The fermentation step is advantageously performed in the presence of at least one microorganism, also known as an acetogenic strain.

Throughout the remainder of the text, the terms "fermentation", "fermentation step", or "fermentation reaction" relate to the conversion of the gases $H_2$, CO and/or $CO_2$ and include both the growth phase of the fermenting microorganism and the phase of production of the molecules of interest, such as alcohols, acids, alcohol acids and/or carboxylic acids by this microorganism.

In point of fact, the capacity of certain microorganisms to grow on gaseous substrates such as carbon monoxide (CO), carbon dioxide ($CO_2$) and/or hydrogen ($H_2$) as sole source of carbon was discovered in 1903. A large number of anaerobic organisms, more particularly "acetogenic" organisms, have this capacity of metabolizing CO and/or the $CO_2/H_2$ pair to produce various final molecules of interest such as acetate, butyrate, ethanol and/or n-butanol.

The microorganisms that are capable of performing this fermentation process are mainly from the genus *Clostridium*, but other microorganisms, for instance those from the genera *Acetobacteria, Butyribacterium, Desulfobacterium, Moorella, Oxobacter* or *Eubacteria*, may also be used for performing this fermentation process.

The microorganisms are therefore chosen so as to lead to production of the desired products in the fermentation step. The fermentation products may include, for example, alcohols and acids.

For example, various patents describe strains that are capable of producing the abovementioned products of interest, starting from synthesis gas. Among the acetogenic strains of the genus *Clostridium*, mention may be made of U.S. Pat. No. 5,173,429 describing a strain of *Clostridium ljungdahlii* (ATCC 49587) which produces ethanol and acetate. Other strains of the same species are described in documents WO 2000/68407, EP 117 309 and U.S. Pat. Nos. 5,173,429, 5,593,886 and 6,368,819, WO 1998/00558 and WO 2002/08438. Certain strains of *Clostridium*, such as the strains of *Clostridium autoethanogenum* (DSM 10061 and DSM 19630) described in documents WO 2007/117 157 and WO 2009/151 342, *Clostridium ragsdalei* (P11, ATCC BAA-622) described in U.S. Pat. No. 7,704,723 or else the strains of *Clostridium carboxidivorans* (ATCC PTA-7827) described in patent application US 2007/0 276 447, are themselves also capable of producing molecules of interest by fermentation starting from gases ($H_2$, CO and/or $CO_2$).

Said acetogenic strain(s) or microorganism(s) used in the fermentation step of the process according to the invention are preferably chosen from the following microorganisms: *Acetogenium kivui, Acetoanaerobium noterae, Acetobacterium woodii, Alkalibaculum bacchi* CP11 (ATCC BAA-1772), *Blautia producta, Butyribacterium methylotrophicum, Caldanaerobacter subterraneus, Caldanaerobacter subterraneus pacificus, Carboxydothermus hydrogenoformans, Clostridium aceticum, Clostridium acetobutylicum, Clostridium acetobutylicum* P262 (DSM 19630 from DSMZ Germany), *Clostridium autoethanogenum* (DSM 19630 from DSMZ Germany), *Clostridium autoethanogenum* (DSM 10061 from DSMZ Germany), *Clostridium autoethanogenum* (DSM 23693 from DSMZ Germany), *Clostridium autoethanogenum* (DSM 24138 from DSMZ Germany), *Clostridium carboxidivorans* P7 (ATCC PTA-7827), *Clostridium coskatii* (ATCC PTA-10522), *Clostridium drakei*, *Clostridium ljungdahlii* PETC (ATCC 49587), *Clostridium ljungdahlii* ER12 (ATCC 55380), *Clostridium ljungdahlii* C-01 (ATCC 55988), *Clostridium ljungdahlii* 0-52 (ATCC 55889), *Clostridium magnum*, *Clostridium pasteurianum* (DSM 525 from DSMZ Germany), *Clostridium ragsdalei* P11 (ATCC BAA-622), *Clostridium scatologenes*, *Clostridium thermoaceticum*, *Clostridium ultunense*, *Desulfotomaculum kuznetsovii*, *Eubacterium limosum*, *Geobacter sulfurreducens*, *Methanosarcina acetivorans*, *Methanosarcina Barkeri*, *Moorrella thermoacetica*, *Moorrella thermoautotrophica*, *Oxobacter pfennigii*, *Peptostreptococcus productus*, *Ruminococcus productus*, *Thermoanaerobacter kivui*, and mixtures thereof.

Moreover, it should be understood that other microorganisms capable of assimilating $H_2$, CO (otherwise known as carboxidotrophs) and/or $CO_2$ as source of carbon may also be used in the fermentation step of the present invention. All of the aforementioned microorganisms are said to be anaerobic, i.e. incapable of growing in the presence of oxygen. However, aerobic microorganisms may also be used, such as microorganisms belonging to the species *Escherichia coli*. Studies have for example demonstrated that it is possible to produce a strain that is genetically modified to express the genes coding for the enzymes responsible for assimilation of CO (genes of the Wood-Ljungdahl metabolic pathway in order to produce molecules of interest, such as isopropanol, starting from an important metabolic intermediate: acetyl CoA (see patent applications WO 2010/071 697 and WO 2009/094 485)). Other genetically modified microorganisms have been described for producing isopropanol, for instance the microorganism *C. ljungdahlii* (see US 2012/0 252 083).

In preferred embodiments, the microorganisms are chosen from *Clostridium autoethanogenum*, *Clostridium ljungdahlii*, *Clostridium aceticum*, *Moorella thermoacetica*, *Acetobacterium woodii* and *Alkalibaculum bacchi* for producing ethanol and/or acetate, *Clostridium autoethanogenum*, *Clostridium ljungdahlii* and *C. ragsdalei* for producing 2,3-butanediol and *Clostridium carboxidivorans*, *Clostridium drakei*, *Clostridium scatologenes* or *Butyribacterium methylotrophicum* for producing butyrate and butanol.

Cultures comprising a mixture of two or more microorganisms may also be used.

The fermentation step may advantageously be performed aerobically or anaerobically and preferably anaerobically.

The fermentation step is advantageously performed in one or more reactors or "bioreactors".

The term "bioreactor" comprises a fermentation device consisting of one or more tanks or tubular reactors, comprising the devices of CSTR or Continuous Stirred Tank Reactor, ICR or Immobilized Cell Reactor, TBR or Trickle Bed Reactor type, fermenters of the Gas Lift type, bubble columns, or a membrane reactor such as the HFMBR or Hollow Fibre Membrane Bio-Reactor system, a static mixer, or any other suitable device for gas-liquid contact.

Preferably, the required concentration of CO and/or $CO_2$ in the culture medium of said fermentation reactor(s) is at least 2.5 mmol/L of CO and/or $CO_2$.

Said RWGS gas enriched in CO and in water originating from the RWGS reactor used as feedstock for the fermentation step, and containing CO, $CO_2$ and $H_2O$, is conveyed into the fermentation reactor(s) in the form of a substrate advantageously containing a CO content of between 48% and 63% by weight of CO, and preferably between 54% and 63% by weight and an $H_2O$ content of between 16% and 31% by weight and preferably between 16% and 24% by weight, the percentages being expressed as weight percentages relative to the total weight of said RWGS gas.

According to a preferred embodiment, the fermentation step comprises a chain of propagation of an acetogenic strain so as to provide a sufficient amount of cells to inoculate a main reactor, said chain of propagation comprising: i) inoculation of the acetogenic strain in a first propagation reactor providing a minimum density of viable cells for a second propagation reactor having a larger volume, and ii) growth of said acetogenic strain in the second reactor to provide a density of cells suitable for inoculating a third propagation reactor, which is the largest in terms of volume. If necessary, the chain of propagation may comprise a larger number of propagation reactors.

The fermentation step also comprises a production step in which the fermentation process is optimum, i.e. in which the molecules of interest are produced in great quantity. The stream comprising at least one oxygenated compound as claimed is therefore produced in said production step.

Preferably, the propagation step may be carried out in one or more reactors for propagation of the microorganism, all of these reactors being connected to allow transfer of the microbial culture.

One or more "production" reactors in which the fermentation process takes place are also employed.

The microorganisms or acetogenic strains are generally cultured until an optimum cell density is obtained for inoculating the production reactors. This level of inoculum may vary from 0.5% to 75%, which makes it possible to have production reactors that are larger than the propagation reactors. Thus, the propagation reactor can be used for seeding several other larger production reactors.

In the case where the fermentation step comprises a propagation step and a production step, the RWGS gas enriched in CO and in water may advantageously be introduced in the fermentation step at the level of the reactors of the production step.

At least one additional carbon-containing substrate may advantageously be used in combination with the CO-enriched RWGS gas, for growing the microorganisms in the propagation step. Said carbon-containing substrate may advantageously be selected from n monosaccharides such as glucose, fructose or xylose, polysaccharides such as starch, sucrose, lactose or cellulose, metabolic intermediates such as pyruvate or any other carbon-containing substrate known by a person skilled in the art that can be assimilated by the microorganisms used in the process. Said carbon-containing substrate may also be a mixture of two or more of these carbon-containing substrates.

Control of the operating conditions is also necessary for optimizing the execution of the fermentation step. By way of example, Lowe et al. (Microbiological Review, 1993, 57: 451-509), or Henstra et al. (Current Opinion in Biotechnology 2007, 18:200-206), summarize the optimum operating conditions in terms of temperatures and pH, for growing the microorganisms usable in the fermentation process. The pH is one of the most important factors for the fermentation activity of the microorganisms used in the process. Preferably, said fermentation step is performed at a pH of between 3 and 9, preferably between 4 and 8, and more preferably between 5 and 7.5.

Temperature is also an important parameter for improving fermentation as it has an influence both on microbial activity and on the solubility of the gases used as substrate. The choice of temperature depends on the microorganism used, certain strains being capable of growing under moderate temperature conditions (strains called mesophiles) and others under high temperature conditions (thermophilic microorganisms). Preferably, said fermentation step is performed at a growth temperature of between 20° C. and 80° C. Preferably, said fermentation step is performed at a growth temperature of between 20° C. and 40° C. for mesophilic strains and preferably between 25° C. and 35° C. and between 40° C. and 80° C. for thermophilic strains, and preferably between 50° C. and 60° C.

The oxidation-reduction potential (otherwise known as the "redox" potential) is also an important parameter to be controlled in the fermentation process. The redox potential is preferably greater than −450 mV and preferably between −150 and −250 mV.

Said fermentation step is moreover advantageously performed at a pressure of between 0.1 and 0.4 MPa.

The nutrient medium or culture medium of the fermentation step may advantageously contain at least one reducing agent so as to improve the performance of the fermentation process by controlling the redox potential of the fermentation step.

The nutrient medium may also comprise minerals, vitamins, metal co-factors or metals specific to the metalloenzymes involved in the pathways for conversion of the gas into products of interest. Anaerobic nutrient media that are suitable for the fermentation of ethanol using CO and/or $CO_2$ as sole source(s) of carbon are known to those skilled in the art. For example, suitable media are described in U.S. Pat. Nos. 5,173,429 and 5,593,886 and WO 02/08438, WO 2007/115 157 and WO 2008/115 080 or the publication J. R. Phillips et al. (Bioresource Technology 190 (2015) 114-121).

The composition of the nutrient medium must allow efficient conversion of the substrate (CO and $CO_2$) to a molecule of interest. This conversion of the substrate is advantageously at least 5% and it may range up to 99%, preferably from 10% to 90%, and preferably 40% to 70%.

The nutrient medium may contain at least one or more sources of nitrogen, one or more sources of phosphorus and one or more sources of potassium. The nutrient medium may comprise one of these three compounds, or any combination of the three, and, in an important aspect, the medium must comprise all three compounds. The source of nitrogen may be chosen from ammonium chloride, ammonium phosphate, ammonium sulfate, ammonium nitrate, and mixtures thereof. The source of phosphorus may be chosen from phosphoric acid, ammonium phosphate, potassium phosphate, and mixtures thereof. The source of potassium may be chosen from potassium chloride, potassium phosphate, potassium nitrate, potassium sulfate, and mixtures thereof.

The nutrient medium may also comprise one or more metals such as iron, tungsten, nickel, cobalt or magnesium; and/or sulfur; and/or thiamine. The medium may comprise any one of these components or any combination, and, in an important aspect, it comprises all of these components. The source of iron may be chosen from ferrous chloride, ferrous sulfate and mixtures thereof. The source of tungsten may be chosen from sodium tungstate, calcium tungstate, potassium tungstate and mixtures thereof. The source of nickel may include a source of nickel chosen from the group consisting of nickel chloride, nickel sulfate, nickel nitrate, and mixtures thereof. The source of cobalt may be chosen from cobalt chloride, cobalt fluoride, cobalt bromide, cobalt iodide and mixtures thereof. The source of magnesium may be chosen from magnesium chloride, magnesium sulfate, magnesium phosphate, and mixtures thereof. The source of sulfur may comprise cysteine, sodium sulfide, and mixtures thereof.

The fermentation step may also advantageously be performed as described in patent applications WO 2007/117 157, WO 2008/115 080, U.S. Pat. Nos. 6,340,581, 6,136,577, 5,593,886, 5,807,722 and 5,821,111.

As mentioned previously, the optimum operating conditions for performing this fermentation step depend partly on the microorganism(s) used. The most important parameters to be controlled are the pressure, the temperature, the gas and liquid flow rate, the pH of the medium, the redox potential, the stirring speed and the level of inoculum. It is also necessary to ensure that the contents of gaseous substrates in the liquid phase are not limiting. Examples of suitable operating conditions are described in patents WO 02/08438, WO 07/117 157 and WO 08/115 080. The ratio between the $H_2$ and the gaseous substrates CO and $CO_2$ may also be large to control the nature of the alcohols produced by the fermenting microorganisms. In patent application WO 12/131 627, it is, for example, described that depending on the level of hydrogen, it is possible to produce either ethanol alone, or ethanol and 2,3-butanediol if the $H_2$ percentage is below 20% (by volume). The typical composition of the purge gas feeding the production reactors would advantageously make it possible to produce 2,3-butanediol and ethanol by *Clostridium autoethanogenum*.

Preferably, fermentation should be performed at a pressure above the ambient pressure. By employing an increased pressure it is possible to substantially increase the rate of transfer of gas to the liquid phase so that it is assimilated by the microorganism as a carbon source. This operation notably makes it possible to reduce the retention time (defined as the volume of liquid in the bioreactor divided by the flow rate of incoming gas) in the bioreactor and thus better productivity (defined as the number of grams of molecules of interest produced per litre and per day of production) of the fermentation process. Examples of productivity improvement are described in patent WO 02/08438.

In accordance with the invention, said fermentation step produces a liquid fermentation stream comprising ethanol. According to one or more embodiments, the liquid fermentation stream comprises at least 80%, preferably at least 90%, very preferably at least 95% by weight of ethanol relative to the total weight of the liquid fermentation stream, for example after concentrating in ethanol the liquid fermentation stream, for example by distillation.

According to one or more embodiments, the liquid fermentation stream produced by the fermentation step may also contain nutrient medium, molecules of interest (alcohols, alcohol acids, acids), i.e. a stream of oxygenated compounds as described below and bacterial cells.

According to one or more embodiments, the liquid fermentation stream comprises ethanol and at least one other oxygenated compound chosen from alcohols containing 2 to 6 carbon atoms, diols containing 2 to 4 carbon atoms, alcohol acids containing 2 to 4 carbon atoms, carboxylic acids containing 2 to 6 carbon atoms, aldehydes containing 2 to 12 carbon atoms and esters containing 2 to 12 carbon atoms, alone or as a mixture.

According to one or more embodiments, the alcohols containing 2 to 6 carbon atoms are chosen from n-propanol, isopropanol, butanol, isobutanol and hexanol, the diols containing 2 to 4 carbon atoms are chosen from 2,3-butylene glycol (2,3-butanediol), the alcohol acids containing 2 to 4 carbon atoms are preferably lactic acid, the carboxylic acids containing 2 to 6 carbon atoms are chosen from acetic acid, butyric acid and hexanoic acid, the aldehydes containing 2 to 12 carbon atoms are chosen from ethanal, propanal, butanal, pentanal, 3-methylbutanal, hexanal, furfural and glyoxal, alone or as a mixture, and the esters containing 2 to 12 carbon atoms and preferably 2 to 6 carbon atoms are chosen from methyl formate, methyl acetate, methyl propanoate, methyl butanoate, methyl pentanoate, ethyl acetate, propyl acetate, isopropyl acetate, butyl acetate, isobutyl acetate and butyl butyrate, alone or as a mixture.

According to one or more embodiments, the liquid fermentation stream comprises at least one oxygenated compound chosen from n-propanol, isopropanol, butanol, isobutanol, hexanol, acetic acid, butyric acid, hexanoic acid, lactic acid and 2,3-butylene glycol (2,3-butanediol), alone or as a mixture.

A hydrogen makeup may advantageously be optionally introduced into said fermentation step in the case where the composition of the feedstock feeding said step does not comprise a sufficient amount of hydrogen. The use of a substrate lean in $H_2$ leads to production of important acids. In point of fact, as mentioned previously, the additional hydrogen supply makes it possible to improve the conversion of the CO present in the fermentation medium into alcohols (according to the balance equations of Bertsch and Müller, Biotechnol. Biofuels (2015) 8: 210) and to promote the conversion of the $CO_2$.

The makeup hydrogen may advantageously come from any process for producing hydrogen, for instance a steam reforming process or a catalytic reforming process, electrolysis of water, dehydrogenation of alkanes, and its hydrogen purity is usually between 75 vol % and 99.9 vol %. This makeup hydrogen is conveyed by line 34.

According to one or more embodiments, at the outlet of the fermentation reaction section 52, $CO_2$ is recycled via line 54 to the inlet of the RWGS reaction section 50, and/or the water produced is at least partly purged via line 55.

At the outlet of the fermentation section 52, the ethanol is recycled via line 35 to the inlet of the pyrolysis unit 13.

Thus, the combination of an RWGS reaction section 50, followed by a fermentation section 52 and by a recycling of the ethanol produced by fermentation to the inlet of the pyrolysis unit 13, makes it possible to produce additional aromatics from the CO and $CO_2$, which are by-products of the pyrolysis unit 13.

The device and the process according to the invention thus enable gains of up to 40% by weight of aromatic compounds.

In the present patent application, the groups of chemical elements are given, by default, according to the CAS classification (CRC Handbook of Chemistry and Physics, published by CRC Press, Editor-in-Chief D. R. Lide, 81st edition, 2000-2001). For example, group VIII according to the CAS classification corresponds to the metals from columns 8, 9 and 10 according to the new IUPAC classification; group VIb according to the CAS classification corresponds to the metals from column 6 according to the new IUPAC classification.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 20/09.871, filed Sep. 29, 2020, are incorporated by reference herein.

EXAMPLES

Example of a Reference Device

Use is made of an example of a reference device for the conversion of a feedstock comprising a mixture of aromatic compounds resulting from a process for the conversion of lignocellulosic biomass based on a conversion by catalytic pyrolysis.

The reference device example is similar to the device represented in FIG. 1, except that the transalkylation unit 8 is replaced with a disproportionation unit. Furthermore, the reference device example does not employ the following units:
heavy aromatics column 7;
selective hydrogenolysis unit 9;
stabilization column 12;
RWGS reaction section 50;
fermentation reaction section 52;

The flow rates of said aromatic compounds of the feedstock to be treated, at the inlet of the reference device, are as follows:
benzene: 2.63 t/h;
toluene: 5.64 t/h;
ethylbenzene: 0.15 t/h; and
xylenes: 3.56 t/h.
i.e., a total of 11.98 t/h of aromatic compounds.

Furthermore, the pyrolysis reaction section produces CO and $CO_2$, which are not converted into other chemical compounds. The flow rate of CO produced is 22.25 t/h and the flow rate of $CO_2$ is 15.99 t/h.

In the reference device, all of the toluene is converted, by a disproportionation unit, into benzene and xylenes. The xylenes of the feedstock and those produced by disproportionation are isomerized to give para-xylene, which is separated from the xylene mixture at thermodynamic equilibrium at the outlet of the isomerization unit, by means of a simulated moving bed adsorption unit. This set of unit operations makes it possible, in the best of cases (assuming a selectivity of 100% for each unit operation), to produce the following compounds:
benzene: 5.02 t/h;
para-xylene: 6.96 t/h
total aromatics: 11.98 t/h.

Example of a Device According to the Invention

The example of a device according to the invention makes it possible to increase the total amount of aromatics produced for the same flow rate of biomass feedstock entering the pyrolysis unit 13 as in the reference device, and in particular to increase the amount of para-xylene produced.

Relative to the scheme of the reference device, the RWGS reaction section 50, the fermentation reaction section 52, the recycling of the $CO_2$ at the outlet of the fermentation reaction section 52 to the inlet of the RWGS reaction section 50 via line 54, and also the recycling of the ethanol produced by the fermentation to the inlet of the pyrolysis unit 13 are notably added.

The pyrolysis gas 32, obtained from the catalytic pyrolysis unit 13, containing CO, $CO_2$ and hydrogen is introduced into the RWGS reaction section 50, with a hydrogen makeup via line 34. At the outlet of the RWGS reaction section 50, the RWGS gas 51 is introduced into a fermentation reaction section 52. At the outlet of the fermentation reaction section 52, the $CO_2$ is recycled to the inlet of the RWGS reaction section 50, and the water produced is purged via line 55. The ethanol produced by the fermentation is recycled via line 35 to the inlet of the pyrolysis unit 13.

The conversion of the CO and $CO_2$ by means of this process may be complete. The water formed may be advantageously used upstream of the pyrolysis unit 13 for the biomass pretreatment operations.

The fermentation thus makes it possible to produce 26.63 t/h of ethanol, which is recycled via line 35 to the inlet of the pyrolysis unit 13.

TABLE 1

|  | Example of a reference device | Example of a device according to the invention |
|---|---|---|
| $H_2$ makeup (t/h) | 0 | 5.222 |
| Inlet of the aromatic complex (t/h) | | |
| C1-C6 paraffins | 0 | 11.60 |
| Benzene | 2.63 | 3.02 |
| Toluene | 5.64 | 7.70 |
| Ethylbenzene | 0.15 | 0.15 |
| Xylenes | 3.56 | 5.48 |
| A9 + A10 aromatics | 0 | 0.45 |
| Products (t/h) | | |
| Benzene | 5.02 | 6.5 |
| p-Xylene | 6.96 | 10.3 |
| Total aromatics | 11.98 | 16.8 |
| C1-C6 paraffins | 0 | 11.60 |
| Water | 0 | 27.38 |
| CO | 22.25 | 0 |
| $CO_2$ | 15.99 | 0 |
| $H_2$ | 0.338 | 0 |

Table 1 shows that the implementation according to the invention makes it possible to produce 40% by weight more of aromatics (17.64 t/h instead of 11.98 t/h). This increase in aromatic compounds essentially concerns the para-xylene, which increases from 6.96 t/h to 11 t/h, i.e. a gain of 58%.

An amount of water equal to 27.38 t/h is also produced, and may be used in the biomass pretreatment steps upstream of the pyrolysis unit.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A device for the conversion of a first hydrocarbon feedstock comprising aromatic compounds, comprising:
   a fractionation train (4-7) suitable for extracting at least one benzene-comprising cut (22), one toluene-comprising cut (23) and one cut comprising xylenes and ethylbenzene (24) from the first hydrocarbon feedstock (2);
   a xylene separation unit (10) suitable for treating the cut comprising xylenes and ethylbenzene (24) and producing an extract (39) comprising para-xylene and a raffinate (40) comprising ortho-xylene, meta-xylene and ethylbenzene;
   an isomerization unit (11) suitable for treating the raffinate (40) and producing an isomerate (42) enriched in para-xylene which is sent to the fractionation train (4-7);
   a pyrolysis unit (13) suitable for treating a second hydrocarbon feedstock (30), producing at least one pyrolysis effluent (31) comprising hydrocarbon compounds having 6 to 10 carbon atoms feeding, at least partially, the first hydrocarbon feedstock (2), and producing a pyrolysis gas (32) comprising at least CO, $CO_2$ and $H_2$;
   a reverse water gas shift RWGS reaction section (50), suitable for treating the pyrolysis gas (32) and producing an RWGS gas (51) enriched in CO and in water;
   a fermentation reaction section (52) suitable for treating the RWGS gas (51) enriched in CO and in water, producing ethanol and recycling the ethanol to the inlet of the pyrolysis unit (13).

2. The conversion device according to claim 1, in which the fermentation reaction section (52) is suitable for recycling $CO_2$ present at the fermentation outlet to the inlet of the RWGS reaction section (50).

3. The conversion device according to claim 1, further comprising a makeup line (34) for providing a supply of $H_2$ to the pyrolysis gas (32).

4. The conversion device according to claim 1, in which the fractionation train (4-7) is suitable for extracting a C9-C10 monoaromatics cut (25) from the first hydrocarbon feedstock (2).

5. The conversion device according to claim 4, further comprising a transalkylation unit (8) suitable for treating the C9-C10 monoaromatics cut (25) with the toluene-comprising cut (23) and producing xylenes which are sent to the fractionation train (4-7).

6. The conversion device according to claim 5, further comprising a selective hydrogenolysis unit (9) suitable for:
   treating the C9-C10 monoaromatics cut (25); and
   producing a hydrogenolysis effluent enriched in methyl-substituted aromatic compounds (46) which is sent to the transalkylation unit (8).

7. The conversion device according to claim 1, further comprising a disproportionation unit suitable for treating, at least in part, the toluene-comprising cut (23) and producing a xylene-enriched cut which is recycled to the isomerization unit (11).

8. A process for conversion of a first hydrocarbon feedstock comprising aromatic compounds, comprising:
   fractionating the first hydrocarbon feedstock (2) in a fractionation train (4-7) in order to extract at least one benzene-comprising cut (22), one toluene-comprising cut (23) and one cut comprising xylenes and ethylbenzene (24);
   separating the cut comprising xylenes and ethylbenzene (24) in a xylene separation unit (10) and producing an extract (39) comprising para-xylene and a raffinate (40) comprising ortho-xylene, meta-xylene and ethylbenzene;
   isomerizing the raffinate (40) in an isomerization unit (11) and producing an isomerate (42) enriched in para-xylene;
   sending the isomerate (42) enriched in para-xylene to the fractionation train (4-7);
   treating a second hydrocarbon feedstock (30) in a pyrolysis unit (13) in order to produce at least one pyrolysis effluent (31) comprising hydrocarbon compounds having 6 to 10 carbon atoms feeding, at least partially, the first hydrocarbon feedstock (2), and producing a pyrolysis gas (32) comprising at least CO, $CO_2$ and $H_2$;

treating the pyrolysis gas (32) in an RWGS reaction section (50), in order to produce an RWGS gas (51) enriched in CO and in water;

treating, at least in part, the RWGS gas (51) enriched in CO and in water in a fermentation reaction section (52) in order to produce ethanol; and recycling the ethanol to the inlet of the pyrolysis unit (13).

9. The conversion process according to claim 8, comprising a step of recycling $CO_2$ present at the fermentation outlet to the inlet of the RWGS reaction section (50).

10. The conversion process according to claim 8, further comprising providing a supply of $H_2$ to the pyrolysis gas (32) by means of a makeup line (34).

11. The conversion process according to claim 8, in which the pyrolysis unit (13) comprises at least one reactor used under at least one of the following operating conditions:

absolute pressure of between 0.1 and 0.5 MPa and HSV of between 0.01 and 10 $h^{-1}$, the HSV is the ratio of the volume flow rate of feedstock to the volume of catalyst used;

temperature of between 400° C. and 1000° C.;

zeolite catalyst.

12. The conversion process according to claim 8, in which the RWGS reaction section (50) comprises at least one reactor used under at least one of the following operating conditions:

temperature of between 400° C. and 800° C.;

pressure of between 0.1 and 10 MPa;

space velocity of the gas at the inlet of the reactor of between 5000 and 20 000 $mL/g_{cata}/h$;

catalysts based on iron or alkali metals.

13. The conversion process according to claim 8, in which the fermentation reaction section (52) comprises at least one reactor used under at least one of the following operating conditions:

presence of a microorganism capable of metabolizing the CO and/or the $CO_2/H_2$ pair to produce ethanol;

pH of between 3 and 9;

growth temperature of between 20° C. and 80° C.;

redox potential of greater than −450 mV;

pressure of between 0.1 and 0.4 MPa.

14. The conversion process according to claim 8, in which the isomerization unit (11) comprises a gas-phase isomerization zone and/or a liquid-phase isomerization zone, in which the gas-phase isomerization zone is used under at least one of the following operating conditions:

temperature of greater than 300° C.;

pressure of less than 4.0 MPa;

hourly space velocity of less than 10 $h^{-1}$;

hydrogen-to-hydrocarbon molar ratio of less than 10;

in the presence of a catalyst comprising at least one zeolite having channels whose opening is defined by a ring of 10 or 12 oxygen atoms, and at least one group VIII metal in a content of between 0.1% and 0.3% by weight, limits included, and in which the liquid-phase isomerization zone is used under at least one of the following operating conditions:

temperature of less than 300 C;

pressure of less than 4 MPa;

hourly space velocity of less than 10 $h^{-1}$;

in the presence of a catalyst comprising at least one zeolite having channels whose opening is defined by a ring of 10 or 12 oxygen atoms.

15. The conversion process according to claim 11, wherein said at least one reactor is operated under at least one of the following operating conditions:

HSV of between 0.01 and 5 $h^{-1}$; and temperature of between 400° C. and 650° C.

16. The conversion process according to claim 11, wherein said at least one reactor is operated under at least one of the following operating conditions:

HSV of between 0.1 and 3 $h^{-1}$; and temperature of between 450° C. and 600° C.

17. The conversion process according to claim 12, wherein said at least one reactor is operated under at least one of the following operating conditions:

temperature of between 500° C. and 800° C.; and pressure of between 0.1 and 5 MPa.

18. The conversion process according to claim 12, wherein said at least one reactor is operated under at least one of the following operating conditions:

temperature of between 650° C. and 750° C.; and pressure of between 0.1 and 2.5 MPa.

19. The conversion process according to claim 11, wherein said zeolite is selected from ZSM-5, ferrierite, zeolite beta, zeolite Y, mordenite, ZSM-23, ZSM-57, EU-1 and ZSM-11.

20. The conversion process according to claim 15, wherein said zeolite is selected from ZSM-5, ferrierite, zeolite beta, zeolite Y, mordenite, ZSM-23, ZSM-57, EU-1 and ZSM-11.

21. The conversion process according to claim 16, wherein said zeolite is selected from ZSM-5, ferrierite, zeolite beta, zeolite Y, mordenite, ZSM-23, ZSM-57, EU-1 and ZSM-11.

* * * * *